US011291697B2

(12) United States Patent
Wang et al.

(10) Patent No.: US 11,291,697 B2
(45) Date of Patent: *Apr. 5, 2022

(54) PROBIOTIC COMPOSITION AND USE THEREOF

(71) Applicant: INFINITUS (CHINA) COMPANY LTD., Guangdong (CN)

(72) Inventors: Yuanyuan Wang, Guangdong (CN); Wei Chen, Guangdong (CN); Gang Wang, Guangdong (CN); Xiaofeng Zhu, Guangdong (CN); Fangli Ma, Guangdong (CN); Junyong Xiao, Guangdong (CN); Hao Zhang, Guangdong (CN); Jianxin Zhao, Guangdong (CN)

(73) Assignee: INFINITUS (CHINA) COMPANY LTD., Guangdong (CN)

( * ) Notice: Subject to any disclaimer, the term of this patent is extended or adjusted under 35 U.S.C. 154(b) by 91 days.

This patent is subject to a terminal disclaimer.

(21) Appl. No.: 16/520,359

(22) Filed: Jul. 24, 2019

(65) Prior Publication Data

US 2020/0261515 A1  Aug. 20, 2020

(30) Foreign Application Priority Data

Feb. 20, 2019  (CN) .......................... 201910126879.7

(51) Int. Cl.
*A61K 35/745* (2015.01)
*A23L 33/135* (2016.01)
(Continued)

(52) U.S. Cl.
CPC .......... *A61K 35/745* (2013.01); *A23L 33/135* (2016.08); *A61K 35/747* (2013.01); *A61P 1/00* (2018.01)

(58) Field of Classification Search
CPC ................ A61K 35/745; A61K 35/747; A61K 2300/00; A61K 9/19; A61K 47/26; A61K 9/0095; A61K 9/10; A61K 9/1605; A61K 9/2004; A61K 9/4841; A61K 31/733; A61K 2035/115; A61K 31/00; A61K 35/74; A61K 35/741; A61K 35/742; A61K 45/06; A61K 9/0053; A61K 9/2846; A61K 9/48; A61K 9/4816; A61K 9/4891; A23V 2002/00; A23V 2200/30; A23V 2200/3262; A23V 2200/328; A23V 2200/332; A23V 2200/3202; A23V 2200/3204; A23V 2200/326; A23V 2200/324; A23V 2200/31; A23L 33/135; A23L 33/00; A23L 11/09; A23L 19/00; A23L 29/065; A23L 33/175; A23L 2/52; A23L 2/02; A23L 2/382; A23L 33/21; A23L 11/50; A23Y 2220/71; A23Y 2220/73; A23Y 2300/19; A23Y 2220/17; A23Y 2220/05; A23Y 2220/37; A23Y 2300/21; A61P 3/00; A61P 1/00; A61P 29/00; A61P 39/06; A61P 3/04; A61P 3/06; A61P 3/10; A61P 25/00; A61P 43/00; A61P 17/00; A61P 9/10; A61P 19/02; A61P 1/12; A61P 1/16; A61P 25/22; A61P 25/24; A61P 25/28; A61P 37/02; A61P 39/00; A61P 3/08; C12N 1/20; C12N 1/205; A23C 13/16; A23C 19/0323; A23C 19/062; A23C 9/1234; A23C 11/06; C12R 1/01; C12R 1/225; C12R 2001/01; C12Q 1/689; G01N 2333/605; G01N 2800/04; G01N 33/66

See application file for complete search history.

(56) References Cited

U.S. PATENT DOCUMENTS 9,486,487 B2 * 11/2016 Cutcliffe .............. A61K 35/742
10,022,408 B2 * 7/2018 Leser ...................... A61P 25/22
(Continued)

FOREIGN PATENT DOCUMENTS

| CN | 103446139 A | 12/2013 |
|---|---|---|
| CN | 103596949 A | 2/2014 |

(Continued)

OTHER PUBLICATIONS

First Office Action dated Mar. 3, 2020 for Chinese patent application No. 201910126879.7, English translation provided by Global Dossier.
Guo Jun-Xia et al., "Research advances in probiotics and metabolic syndrome", Journal of Food Safety and Quality, vol. 5 No. 6, Jun. 30, 2014, p. 1583-1588.
Wang Jing-jing et al., "Modulation of gut microbiota during probiotic-mediated attenuation of metabolic syndrome in high fat diet-fed mice", The ISME Journal (2015) 9, p. 1-15.

*Primary Examiner* — Deborah K Ware
(74) *Attorney, Agent, or Firm* — Yue (Robert) Xu; Apex Attorneys at Law, LLP

(57) ABSTRACT

The present disclosure relates to the field of microbial technology, and discloses a probiotic composition and use thereof. The probiotic composition in the present disclosure is consisted of *Bifidobacterium adolescentis* CCFM8630, *Lactobacillus reuteri* CCFM8631 and *Lactobacillus rhamnosus* CCFM1044, whose effect of alleviating metabolic syndrome is significantly better than that of CCFM8630 or CCFM8631 alone or combination of the two, especially in aspects of lowering epididymal fat content, lowering fasting blood glucose level, lowering the area under sugar tolerance curve and lowering contents of serum low density lipoprotein and total cholesterol, improving liver antioxidant capacity and lowering serum IL-1β content, etc. The extent of decrease or increase is increased by 9.62% to 769.62% compared with formulations of a single probiotic or a combination of two probiotics. The combination of three probiotics achieves a significant synergistic effect.

8 Claims, 5 Drawing Sheets

(51) Int. Cl.
*A61P 1/00* (2006.01)
*A61K 35/747* (2015.01)

(56) References Cited

U.S. PATENT DOCUMENTS

| | | | | |
|---|---|---|---|---|
| 10,245,291 B2* | 4/2019 | Nakamura | ................ | A61P 3/08 |
| 10,675,312 B2* | 6/2020 | Cutcliffe | .............. | A61K 31/733 |
| 10,842,830 B2* | 11/2020 | Cutcliffe | .............. | A61K 31/733 |
| 10,842,831 B2* | 11/2020 | Cutcliffe | ................ | A61K 35/74 |
| 2015/0051204 A1 | 2/2015 | Agreda Navajas et al. | | |
| 2016/0143963 A1* | 5/2016 | Martorell Guerola | ....................... | A23C 11/106 |
| | | | | 424/93.4 |
| 2017/0252382 A1* | 9/2017 | Leser | ....................... | A61P 3/04 |
| 2019/0112674 A1 | 4/2019 | Wang et al. | | |
| 2019/0112675 A1 | 4/2019 | Ma et al. | | |

FOREIGN PATENT DOCUMENTS

| | | | |
|---|---|---|---|
| CN | 103656076 A | | 3/2014 |
| CN | 103977014 A | | 8/2014 |
| CN | 104055012 A | | 9/2014 |
| CN | 105995972 A | | 10/2016 |
| CN | 107523526 A | | 12/2017 |
| CN | 107699517 A | | 2/2018 |
| CN | 108295098 A | | 7/2018 |
| KR | 20150068670 A | | 6/2015 |
| WO | 2018/065132 A1 | | 4/2018 |

\* cited by examiner

PROBIOTIC COMPOSITION AND USE THEREOF

CROSS REFERENCE TO RELATED APPLICATIONS

This application claims the priority of Chinese Patent Application No. 201910126879.7, filed on Feb. 20, 2019, and titled with "PROBIOTIC COMPOSITION AND USE THEREOF", and the disclosures of which are hereby incorporated by reference.

FIELD

The present disclosure relates to the field of microbial technology, specifically to a probiotic composition and uses thereof, especially to a probiotic composition for alleviating metabolic syndrome and uses thereof.

BACKGROUND

Metabolic syndrome is a group of diseases closely related to obesity, diabetes, hypertension and cardiovascular diseases. The clinical manifestations are abnormal glucose tolerance, overweight or obesity, dyslipidemia, and hypertension, etc. Numerous studies have shown that metabolic syndrome is a major cause of cardiovascular disease. People with metabolic syndrome are also more likely to develop an inflammation, and are also susceptible to other diseases, such as polycystic ovarian syndrome, fatty liver, cholesterol gallstone, asthma, abnormal sleep and certain cancers. In addition, metabolic syndrome has a significant relationship with the prevalence rate and mortality of coronary atherosclerotic heart disease and type 2 diabetes. Currently, the prevalence rate of metabolic syndrome worldwide is rapidly increasing, including in developing countries. A population survey conducted in China found that the prevalence rate of metabolic syndrome in population of mainland China in 2016 was 24.5%. Another study showed that the prevalence rate of metabolic syndrome increased from 13.6% in 1993-1996 to 25.5% in 2005-2008.

The treatment of metabolic syndrome is mainly to control and improve the risk factors. The traditional treatment method is drug therapy. For example, CN103977014A discloses a drug for treating metabolic syndrome, including Akebia saponin and curcumin, which can prevent and treat metabolic syndrome by regulating the metabolic processes of proteins, lipids and carbohydrates of patients. CN103596949A discloses a novel compound molecular structure which has a therapeutic effect on diabetes and metabolic syndrome. CN103446139A discloses a pharmaceutical combination for treating metabolic syndrome, including puerarin, cinnamic acid and berberine hydrochloride, and the combination has effects of improving insulin resistance and at the same time lowering blood glucose, lowering blood pressure, lowering blood lipid and improving abdominal obesity. Although drug treatment is effective, it is accompanied by a certain degree of side effects, and it requires a long-term medication, and the body is prone to drug dependence.

A large number of studies have reported that the intestinal flora plays an extremely important role in the physiological metabolism of human body. The structural imbalance of intestinal flora is associated with a variety of diseases, including gastrointestinal diseases (irritable bowel syndrome and inflammatory bowel disease, etc.), metabolic diseases (obesity, hyperlipidemia, diabetes, etc.). The occurrence of metabolic syndrome is also closely related to the imbalance of intestinal flora. The commonly used intestinal flora regulating preparations include probiotics and prebiotics, etc. For example, CN107699517A discloses a *Bifidobacterium adolescentis* and uses thereof, which significantly improves the pathological damage of liver and duodenum, the increase of contents of triglyceride and total cholesterol in serum and oral glucose tolerance of rats with metabolic syndrome caused by high-sugar and high-fat diet. CN107523526A discloses a *Lactobacillus reuteri* and uses thereof, which can reduce levels of lipid and blood glucose in serum of rats with metabolic syndrome. CN108295098A discloses a synbiotic composition for assisting to lower blood glucose, which comprises prebiotics and probiotics, and stimulates the immune function of intestinal tract to restore the intestinal function to normal, maintain the microecological balance of human body, and achieve the effect of lowering blood glucose. CN103656076A discloses a probiotic-Chinese herbal medicine compound preparation having a function of lowering blood glucose. However, all the above patents use a single probiotic or a combination of probiotics and prebiotics or Chinese herbal medicines to alleviate the metabolic syndrome. At present, there are few studies on probiotics compounding formulations of multiple strains that can synergistically improve metabolic syndrome.

SUMMARY

In view of this, an object of the present disclosure is to provide a probiotic composition, which can be used for alleviating metabolic syndrome.

In order to achieve the object of the present disclosure, the following technical solutions are used in the present disclosure.

A probiotic composition, consisting of *Bifidobacterium adolescentis* CCFM8630, *Lactobacillus reuteri* CCFM8631 and *Lactobacillus rhamnosus* CCFM1044 is provided.

Preferably, ratio of viable count of the *Bifidobacterium adolescentis* CCFM8630, the *Lactobacillus reuteri* CCFM8631 and the *Lactobacillus rhamnosus* CCFM1044 is 1:(1-10):(1-10).

In the present disclosure, a method for preparing the probiotic composition is also provided, comprising, respectively inoculating bacteria solutions of *Bifidobacterium adolescentis* CCFM8630, *Lactobacillus reuteri* CCFM8631 and *Lactobacillus rhamnosus* CCFM1044 to modified MRS culture mediums, culturing at 35 to 37° C. under anaerobic conditions for 18-24 h, and collecting thalli; respectively resuspending the thalli with a freeze-drying protective agent so that the content of each thallus is above $10^{10}$ CFU/mL, then culturing the suspension at 37° C. under anaerobic conditions for 40-60 min, drying to obtain freeze-dried bacterial powders of each thallus, resuspending and diluting, and spreading on a plate to determine the viable count in the bacterial powder; and compounding and mixing the freeze-dried bacterial powder of *Bifidobacterium adolescentis* CCFM8630, the freeze-dried bacterial powder of *Lactobacillus reuteri* CCFM8631 and the freeze-dried bacterial powder of *Lactobacillus rhamnosus* CCFM1044 in a certain proportion to achieve a desired ratio of viable count.

Preferably, the modified MRS (mMRS) culture medium is an MRS culture medium that contains 0.05% of L-cysteine hydrochloride; the freeze-drying protective agent is an aqueous solution that contains 100 g/L-150 g/L skimmed milk powder, 30 g/L-100 g/L sucrose and 30 g/L-100 g/L trehalose; and the drying is a vacuum freeze drying that is carried out after pre-freezing at −15 to 20° C. for 8 to 14 h.

In the present disclosure, use of the probiotic composition in the preparation of products for alleviating metabolic syndrome is also provided.

Preferably, the product is a health care food or a medicine.

Preferably, the health care food is a microbial agent or a fermented food.

In the present disclosure, a microbial agent containing the probiotic composition is also provided.

Preferably, viable count of the probiotic composition is more than $1 \times 10^{11}$ CFU/g.

The present disclosure has the following beneficial technical effects: the probiotic composition consisting of *Bifidobacterium adolescentis* CCFM8630, *Lactobacillus reuteri* CCFM8631 and *Lactobacillus rhamnosus* CCFM1044 in the present disclosure is a natural, safe micro-ecological preparation that can effectively alleviate metabolic syndrome, whose effect of alleviating metabolic syndrome is significantly better than that of CCFM8630 or CCFM8631 alone or combination of CCFM8630 and CCFM8631, especially in aspects of lowering epididymal fat content, lowering fasting blood glucose level, lowering the area under sugar tolerance curve and lowering contents of serum low density lipoprotein and total cholesterol, improving liver antioxidant capacity and lowering serum IL-1β content, etc. The extent of decrease or increase is increased by 9.62% to 769.62% compared with formulations of a single CCFM8630 or CCFM8631 or a combination of the two. The combination of three probiotics, *Bifidobacterium adolescentis* CCFM8630, *Lactobacillus reuteri* CCFM8631 and *Lactobacillus rhamnosus* CCFM1044, can achieve a significant synergistic effect. The probiotic composition in the present disclosure may be used in the preparation of a health care food or a medicine for alleviating metabolic syndrome, which has a very broad application prospect.

DESCRIPTION OF MICROBIOLOGICAL PRESERVATION

CCFM8630, classified nomenclature: *Bifidobacterium adolescentis*, is preserved at the General Microbiology Center of the China Microbial Culture Preservation Committee on Jul. 7, 2017; the preservation address is Institute of Microbiology, Chinese Academy of Sciences, No. 3 in No. 1 Yard, Beichen West Road, Chaoyang District, Beijing, China; the preservation number is CGMCC 14395.

CCFM8631, classified nomenclature: *Lactobacillus reuteri*, is preserved at the General Microbiology Center of the China Microbial Culture Preservation Committee on Jul. 7, 2017; the preservation address is Institute of Microbiology, Chinese Academy of Sciences, No. 3 in No. 1 Yard, Beichen West Road, Chaoyang District, Beijing, China; the preservation number is CGMCC 14394.

CCFM1044, classified nomenclature: *Lactobacillus rhamnosus*, is preserved at Guangdong Provincial Microbial Culture Collection on Jan. 21, 2019; the preservation address is Guangdong Institute of Microbiology, 5th Floor, Building 59, No. 100 Yard, Xianlie Middle Road, Guangzhou; the preservation number is GDMCC No: 60540.

BRIEF DESCRIPTION OF DRAWINGS

In order to more clearly illustrate the embodiments of the present invention or the technical solutions in the prior art, the figures to be used in the embodiments or the prior art will be briefly described below.

DETAILED DESCRIPTION

Figure 1:
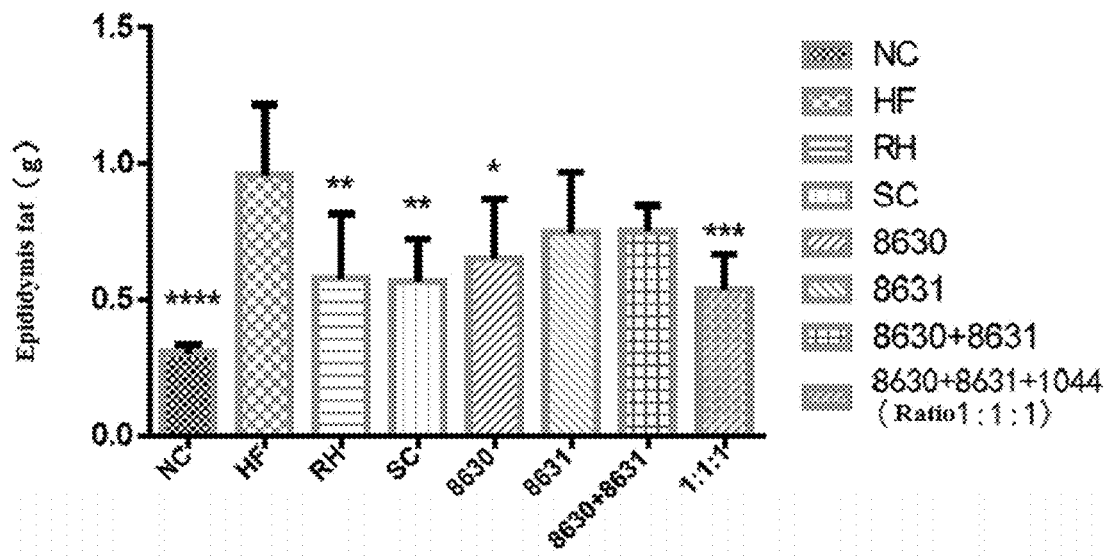
FIG. 1 is a graph showing the effect of different probiotic compounding intervention groups in Example 3 of the present disclosure on alleviating epididymal fat content increasing in mice having high-fat diet induced metabolic syndrome.

In the present disclosure, a probiotic composition and uses thereof are disclosed. One of ordinary skill in the art can learn from the contents of this document and appropriately improve the process parameters. It should be specially indicated that all such alternatives and modifications are obvious to one of ordinary skill in the art and are considered to be included in the present disclosure. The methods and products of the present disclosure have been described in preferred embodiments. It will be apparent that one of ordinary skill in the art can change or appropriately modify and combine the methods described herein to implement and apply the present invention without departing from the content, spirit and scope of the disclosure.

In order to achieve the objects of the present disclosure, the following technical solutions are used in the present disclosure.

A probiotic composition consisting of *Bifidobacterium adolescentis* CCFM8630, *Lactobacillus reuteri* CCFM8631 and *Lactobacillus rhamnosus* CCFM1044 is provided.

The *Bifidobacterium adolescentis* CCFM8630 in the present disclosure is preserved at the General Microbiology Center of the China Microbial Culture Preservation Committee on Jul. 7, 2017; the preservation address is Institute of Microbiology, Chinese Academy of Sciences, No. 3 in No. 1 Yard, Beichen West Road, Chaoyang District, Beijing, China; the preservation number is CGMCC 14395.

The *Lactobacillus reuteri* CCFM8631 in the present disclosure is preserved at the General Microbiology Center of the China Microbial Culture Preservation Committee on Jul. 7, 2017; the preservation address is Institute of Microbiology, Chinese Academy of Sciences, No. 3 in No. 1 Yard, Beichen West Road, Chaoyang District, Beijing, China; the preservation number is CGMCC 14394.

The *Lactobacillus rhamnosus* CCFM1044 in the present disclosure is preserved at Guangdong Provincial Microbial Culture Collection on Jan. 21, 2019; the preservation address is Guangdong Institute of Microbiology, 5th Floor, Building 59, No. 100 Yard, Xianlie Middle Road, Guangzhou; the preservation number is GDMCC No: 60540.

Wherein, preferably, the ratio of viable count of *Bifidobacterium adolescentis* CCFM8630, *Lactobacillus reuteri* CCFM8631 and *Lactobacillus rhamnosus* CCFM1044 in the probiotic composition is 1:(1-10):(1-10).

In some embodiments, the ratio of viable count of *Bifidobacterium adolescentis* CCFM8630, *Lactobacillus reuteri* CCFM8631 and *Lactobacillus rhamnosus* CCFM1044 in the probiotic composition is 1:1:1, 1:5:5, 1:2:10 or 1:10:2.

In the present disclosure, a method for preparing the probiotic composition is also provided, comprising, respectively inoculating bacteria solutions of *Bifidobacterium adolescentis* CCFM8630, *Lactobacillus reuteri* CCFM8631 and *Lactobacillus rhamnosus* CCFM1044 to modified MRS culture mediums, culturing at 35-37° C. under anaerobic conditions for 18-24 h, and collecting thalli; respectively resuspending the thalli with a freeze-drying protective agent so that the content of each thallus is above $10^{10}$ CFU/mL, then culturing the suspension at 37° C. under anaerobic conditions for 40-60 min, drying to obtain freeze-dried bacterial powders of each thallus, resuspending and diluting, and spreading on a plate to determine the viable count in the bacterial powder; and compounding and mixing the freeze-dried bacterial powder of *Bifidobacterium adolescentis* CCFM8630, the freeze-dried bacterial powder of *Lactobacillus reuteri* CCFM8631 and the freeze-dried bacterial powder of *Lactobacillus rhamnosus* CCFM1044 in a certain proportion to achieve a desired ratio of viable count.

In the method for preparing the probiotic composition of the present disclosure, the modified MRS (mMRS) culture medium is an MRS culture medium that contains 0.05% of L-cysteine hydrochloride. The specific preparation method is mixing tryptone 10 g, beef extract 10 g, yeast powder 5 g, glucose 20 g, sodium acetate 5 g, diammonium hydrogen citrate 2 g, dipotassium hydrogen phosphate 2 g, magnesium sulfate heptahydrate 0.5 g, Tween 80 1 mL, manganese sulfate monohydrate 0.25 g and cysteine hydrochloride 0.5 g, and adjusting the volume to 1000 mL with water, adjusting the pH to 6.8, and sterilizing at 119-123° C. for 15-25 min.

In the method of the present disclosure, the freeze-drying protective agent is an aqueous solution that contains 100 g/L-150 g/L skimmed milk powder, 30 g/L-100 g/L sucrose and 30 g/L-100 g/L trehalose. That is, the freeze-drying protective agent is consisted of skimmed milk powder, glucose, trehalose and water, wherein the concentration of skimmed milk powder is 100 g/L-150 g/L, the concentration of glucose is 30 g/L-100 g/L, and the concentration of trehalose is 30 g/L-100 g/L.

Preferably, in the method of the present disclosure, after culturing in the modified MRS culture medium, the collected thalli are washed with phosphate buffer solution for 2 to 4 times, and the phosphate buffer has a pH of 6.8 to 7.2.

In the method of the present disclosure, the drying may be carried out by any bacteria solution drying process, for example vacuum freeze drying. In some embodiments, the drying in the method of the present disclosure is vacuum freeze drying that is carried out after pre-freezing at −15 to 20° C. for 8 to 14 h.

In some embodiments, the method for preparing the probiotic composition in the present disclosure comprises the following steps.

(1) Preparing a Modified MRS Culture Medium (mMRS)

Tryptone 10 g, beef extract 10 g, yeast powder 5 g, glucose 20 g, sodium acetate 5 g, diammonium hydrogen citrate 2 g, dipotassium hydrogen phosphate 2 g, magnesium sulfate heptahydrate 0.5 g, Tween 80 1 mL, manganese sulfate monohydrate 0.25 g and cysteine hydrochloride 0.5 g are added into 1 L water, and adjusting the pH of the culture medium to 6.8 to 7.0.

(2) Preparing A Freeze-Drying Probiotic Protective Agent.

100 g-150 g skimmed milk powder, 30 g-100 g sucrose and 30 g-100 g trehalose are added into 1 L water.

(3) Preparing Freeze-Dried Bacterial Powders.

*Bifidobacterium adolescentis* CCFM8630, *Lactobacillus reuteri* CCFM8631 and *Lactobacillus rhamnosus* CCFM1044 are respectively taken from a strain preservation tube, streaked on a solid culture medium plate to obtain a single colony, and cultured in an anaerobic workstation at 35-37° C. for 36 h-48 h. Single colonies are respectively picked and inoculated into modified MRS liquid culture medium, cultured in the anaerobic workstation at 34-39° C. for 18 h-24 h, and then respectively inoculated in larger volume of liquid culture medium in an inoculum size of 2% to 4% (v/v). After culturing in an anaerobic workstation at 34-39° C. for 18 h-24 h, the resultants are centrifuged at 5000 rpm for 15 min to obtain a bacterial sludge. The bacterial sludge is washed with phosphate buffer (pH 6.8 to 7.2) for 2 to 3 times, and resuspended with freeze-drying protective agent having a mass equal to the bacterial sludge, so that the content of the thalli reaches 1010 CFU/mL or more. Thereafter, the suspension is pre-incubated under anaerobic conditions at 37° C. for 40 to 60 min, and then pre-freezed at −15 to −20° C. for 8 to 14 h, and finally vacuum freeze-drying is carried out to respectively obtain the freeze dried bacterial powders of *Bifidobacterium adolescentis* CCFM8630, *Lactobacillus reuteri* CCFM8631 and *Lactobacillus rhamnosus* CCFM1044.

(4) Preparing the Probiotic Composition.

The *Bifidobacterium adolescentis* CCFM8630, *Lactobacillus reuteri* CCFM8631 and *Lactobacillus rhamnosus* CCFM1044 are compounded and mixed in a certain proportion to achieve a desired ratio of viable count.

In some embodiments, the present invention studies the effect of probiotic composition consisting of *Bifidobacterium adolescentis* CCFM8630, *Lactobacillus reuteri*

CCFM8631 and *Lactobacillus rhamnosus* CCFM1044 on metabolic syndrome. The results show that compared with CCFM8630 or CCFM8631 alone and combination of CCFM8630 and CCFM8631, the probiotic composition consisting of three probiotics, compounding two probiotics CCFM8630 and CCFM8631 with *Lactobacillus rhamnosus* CCFM1044, has a significantly better metabolic syndrome alleviating effect, especially in aspects of lowering epididymal fat content, lowering fasting blood glucose level, lowering the area under sugar tolerance curve and lowering contents of serum low density lipoprotein and total cholesterol, improving liver antioxidant capacity and lowering serum IL-1β content, etc. The extent of decrease or increase is increased by 9.62%-769.62% compared with formulations of a single CCFM8630 or CCFM8631 or a combination of the two. The combination of three probiotics, *Bifidobacterium adolescentis* CCFM8630, *Lactobacillus reuteri* CCFM8631 and *Lactobacillus rhamnosus* CCFM1044, can achieve a significant synergistic effect.

Thus the present disclosure provides use of the probiotic composition in the preparation of products for alleviating metabolic composition.

Therein, the metabolic syndrome is obesity, abnormal blood glucose or blood lipid, inflammation and oxidative stress, etc.

The product includes but is not limited to a health care food or a medicine.

In the product of the present disclosure, daily total intake viable count of the three probiotics is not less than $2 \times 10^8$ CFU.

Therein, the health care food includes but is not limited to a microbial agent or a fermented food.

Further, the present disclosure provides a microbial agent containing the probiotic composition.

Preferably, viable count of the probiotic composition in the microbial agent is not less than $1 \times 10^{11}$ CFU/g.

In the present disclosure, the microbial agent may be prepared by a conventional method.

The present disclosure also provides a fermented food, which is produced by fermenting using the above probiotic composition as a fermenting agent.

The fermented food is fermented dairy products, fermented bean products, or fermented fruit and vegetable products.

The fermented dairy products include but are not limited to yogurt, sour cream and cheese. The fermented bean products include but are not limited to soymilk, fermented soya beans, and soybean paste. The fruit and vegetables in the fermented fruit and vegetable products include but are not limited to cucumber, carrot, beet, celery and cabbage.

The present disclosure also provides a pharmaceutical formulation, comprising an effective amount of the probiotic composition and a pharmaceutically acceptable adjuvant.

The pharmaceutically acceptable adjuvant includes one or more of filler, binder, wetting agent, disintegrant, lubricant, and flavoring agent.

In some embodiments of the present disclosure, the pharmaceutical formulation is in the form of granule, capsule, tablet, pill or oral solution.

The present disclosure has the following beneficial technical effects:
the probiotic composition consisting of *Bifidobacterium adolescentis* CCFM8630, *Lactobacillus reuteri* CCFM8631 and *Lactobacillus rhamnosus* CCFM1044 in the present disclosure is a natural, safe micro-ecological preparation that can effectively alleviate metabolic syndrome, whose effect of alleviating metabolic syndrome is significantly better than that of CCFM8630 or CCFM8631 alone or combination of CCFM8630 and CCFM8631, especially in aspects of lowering epididymal fat content, lowering fasting blood glucose level, lowering the area under sugar tolerance curve and lowering contents of serum low density lipoprotein and total cholesterol, improving liver antioxidant capacity and lowering serum IL-1β content, etc. The extent of decrease or increase is increased by 9.62% to 769.62% compared with formulations of a single CCFM8630 or CCFM8631 or a combination of the two. The combination of three probiotics, *Bifidobacterium adolescentis* CCFM8630, *Lactobacillus reuteri* CCFM8631 and *Lactobacillus rhamnosus* CCFM1044, can achieve a significant synergistic effect. The probiotic composition in the present disclosure may be used in the preparation of a health care food or a medicine for alleviating metabolic syndrome, which has a very broad application prospect.

In order to further understand the present disclosure, the technical solutions in the embodiments of the present disclosure will be clearly and completely described hereinafter in conjunction with the embodiments of the present disclosure. It is apparent that the described embodiments are only a part of the embodiments of the present disclosure, and not all of the embodiments. All other embodiments obtained by one of ordinary skill in the art based on the embodiments of the present disclosure without creative efforts are within the scope of protection of the present disclosure.

Unless otherwise stated, the reagents involved in the embodiments of the present invention are all commercially available products, which are all commercially available.

Example 1: Probiotic Composition has Good Tolerance to Simulated Gastric and Intestinal Fluid The *Bifidobacterium adolescentis* CCFM8630, *Lactobacillus reuteri* CCFM8631 and *Lactobacillus rhamnosus* CCFM1044 preserved under a condition of −80° C. were respectively inoculated to modified MRS (mMRS) culture mediums, cultured in an anaerobic workstation at 37° C. for 36 h, and subcultured twice in an inoculum size of 2%-4% (v/v). The concentrations of viable bacterium of the *Bifidobacterium adolescentis* CCFM8630, *Lactobacillus reuteri* CCFM8631 and *Lactobacillus rhamnosus* CCFM104 culture solutions were adjusted to $5 \times 10^8$ CFU/mL. 1 mL of the *Bifidobacterium adolescentis* CCFM8630, the *Lactobacillus reuteri* CCFM8631 and the *Lactobacillus rhamnosus* CCFM1044 culture solutions in a concentration of $5 \times 10^8$ CFU/mL were taken and mixed evenly. 1 mL of the mixed culture solution was taken and mixed with 9.0 mL simulated gastric fluid (mMRS culture medium containing 1% pepsin, having a pH of 2.5), and cultured under anaerobic conditions at 37° C. Samples were taken at $0^{th}$ h, $0.5^{th}$ h, $1^{st}$ h and $2^{nd}$ h, and spread and cultured on an mMRS solid culture medium, and plate colony counting was carried out, viable count was determined, and survival rate was calculated. The survival rate was a ratio of the logarithm of the viable count at the time of sampling in the culture solution to the logarithm of the viable count at the $0^{th}$ hour, expressed in %. The experimental results were shown in Table 1.

1 mL mixed culture solution was taken and added into 9 mL simulated intestinal fluid (containing 0.3% cholate, 1% trypsin, and mMRS culture medium having a pH of 8), and cultured under anaerobic conditions at 37° C. Samples were taken at $0^{th}$ h, $0.5^{th}$ h, $1^{st}$ h, $2^{nd}$ h, $3^{rd}$ h and $4^{th}$ h, and spread and cultured on an mMRS solid culture medium, and plate colony counting was carried out, viable count was determined, and survival rate was calculated. The survival rate was a ratio of the logarithm of the viable count at the time of sampling in the culture solution to the logarithm of the viable count at the $0^{th}$ hour, expressed in %. The experimental results were shown in Table 2.

TABLE 1

Tolerance of probiotic composition in simulated gastric fluid

| | Simulated gastric fluid | | |
|---|---|---|---|
| Treatment time (h) | 0.5 | 1 | 2 |
| Survival rate (%) | 82.2 | 77.5 | 71.7 |

TABLE 2

Tolerance of probiotic composition in simulated intestinal fluid

| | Simulated intestinal fluid | | | | |
|---|---|---|---|---|---|
| Treatment time (h) | 0.5 | 1 | 2 | 3 | 4 |
| Survival rate (%) | 100 | 100 | 72.3 | 68.4 | 51.9 |

The results showed that the probiotic composition had relatively good tolerance to the simulated gastric fluid and simulated intestinal fluid.

Example 2: Probiotic Composition has No Toxic and Side Effects on C57Bl/6J Mouse The probiotic composition of *Bifidobacterium adolescentis* CCFM8630, *Lactobacillus reuteri* CCFM8631 and *Lactobacillus rhamnosus* CCFM1044 in a ratio of viable count of 1:1:1 was resuspended in a 3% sucrose solution to prepare a bacterial suspension with a concentration of $1.0 \times 10^9$ CFU/mL. 8 healthy male C57BL/6J mice with weights of 20 g-22 g were chosen. After one week of adaptive feeding, the mice were administered intragastrically with bacterial suspension with the above concentration once a day for one week, and the death and body weights were recorded. The experimental results were shown in Table 3.

TABLE 3

Body weight changes and mortality of the mice

| | Time (day) | | | | | | |
|---|---|---|---|---|---|---|---|
| | 1 | 2 | 3 | 4 | 5 | 6 | 7 |
| Weight (g) | 20.2 ± 0.9 | 20.4 ± 1.0 | 20.5 ± 1.3 | 20.7 ± 1.1 | 20.8 ± 0.8 | 21.2 ± 0.9 | 21.6 ± 0.8 |
| Mortality | — | — | — | — | — | — | — |

Note:
—: no mouse died.

The results showed that administration of probiotic composition intragastrically with a concentration of $1.0 \times 10^9$ CFU/mL did not have significant effect on mice: the body weight gain did not change significantly, and no mouse died. The mice were normal in activity and had no obvious pathological appearance.

Example 3: Influence of Probiotic Composition on Epididymal Fat Content and Perirenal Fat Content of Mouse Having High Fat Diet-Induced Metabolic Syndrome The experimental animals were 48 5-week old SPF grade C57BL/6 male mice, which were purchased from Shanghai Slack Laboratory Animal Center. The high fat feed was purchased from Nantong Trophic Animal Feed High-tech Co., Ltd. The model group was fed with TP23300 high fat feed, and the normal control group was fed with TP23302 control feed. After the mice were adaptively feed for 7 days, the experiment started. The animals were given free access to food and water, the temperature was 22±2° C., the humidity was 55±5%, and the illumination was alternately 12 h bright and dark.

The experimental animals were randomly divided into 8 groups: a blank control group (NC), a high fat model control group (HF), a rosiglitazone control group (RH), a simvastatin control group (SC), a *Bifidobacterium adolescentis* CCFM8630 intervention group (8630), a *Lactobacillus reuteri* intervention group (8631), a *Bifidobacterium adolescentis* CCFM8630 and *Lactobacillus reuteri* CCFM8631 compounding group (8630+8631), a *Bifidobacterium adolescentis* CCFM8630, *Lactobacillus reuteri* CCFM8631 and *Lactobacillus rhamnosus* CCFM1044 compounding group (8630+8631+1044). Each group contains 6 mice. The feeding environmental temperature was 20 to 26° C., the humidity was 40% to 70% and the padding was replaced twice a week. In the *Bifidobacterium adolescentis* CCFM8630, *Lactobacillus reuteri* CCFM8631 and *Lactobacillus rhamnosus* CCFM1044 compounding group, the ratio of viable count of *Bifidobacterium adolescentis* CCFM8630, *Lactobacillus reuteri* CCFM8631 and *Lactobacillus rhamnosus* CCFM1044 was 1:1:1. Each mouse was administered intragastrically each day with probiotics in a concentration of $1.0 \times 10^9$ CFU/mL, which was resuspended in 3% sucrose solution, and the volume by intragastric administration was 0.2 mL, i.e., the total amount of probiotics administered to each mouse intragastrically was $2 \times 10^8$ CFU. The experimental groupings and treatment methods were shown in Table 4.

TABLE 4

Grouping of experimental animals

| Group | Number of mouse/group | Treatment time | Feed | Treatment |
|---|---|---|---|---|
| NC | 6 | 20 weeks | Control feed | Administering intragastrically with 0.2 mL 3% sucrose solution each day |
| HF | 6 | 20 weeks | High fat feed | Administering with 0.2 mL 3% sucrose solution each day |

TABLE 4-continued

Grouping of experimental animals

| Group | Number of mouse/group | Treatment time | Feed | Treatment |
| --- | --- | --- | --- | --- |
| RH | 6 | 20 weeks | High fat feed | Administering intragastrically with 0.2 mL 3% sucrose solution each day, which contained 10 mg/kg/BW/d rosiglitazone |
| SC | 6 | 20 weeks | High fat feed | Administering intragastrically with 0.2 mL 3% sucrose solution each day, which contained 3 mg/kg/BW/d simvastatin |
| 8630 | 6 | 20 weeks | High fat feed | Administering intragastrically with 0.2 mL 3% sucrose solution each day, which contained $1.0 \times 10^9$ CFU/mL CCFM8630 |
| 8631 | 6 | 20 weeks | High fat feed | Administering intragastrically with 0.2 mL 3% sucrose solution each day, which contained $1.0 \times 10^9$ CFU/mL CCFM8631 |
| 8630 + 8631 | 6 | 20 weeks | High fat feed | Administering intragastrically with 0.2 mL 3% sucrose solution each day, which contained $1.0 \times 10^9$ CFU/mL CCFM8630 + CCFM8631 |
| 8630 + 8631 + 1044 | 6 | 20 weeks | High fat feed | Administering intragastrically with 0.2 mL 3% sucrose solution each day, which contained $1.0 \times 10^9$ CFU/mL CCFM8630 + CCFM8631 + CCFM1044 |

Figure 2:
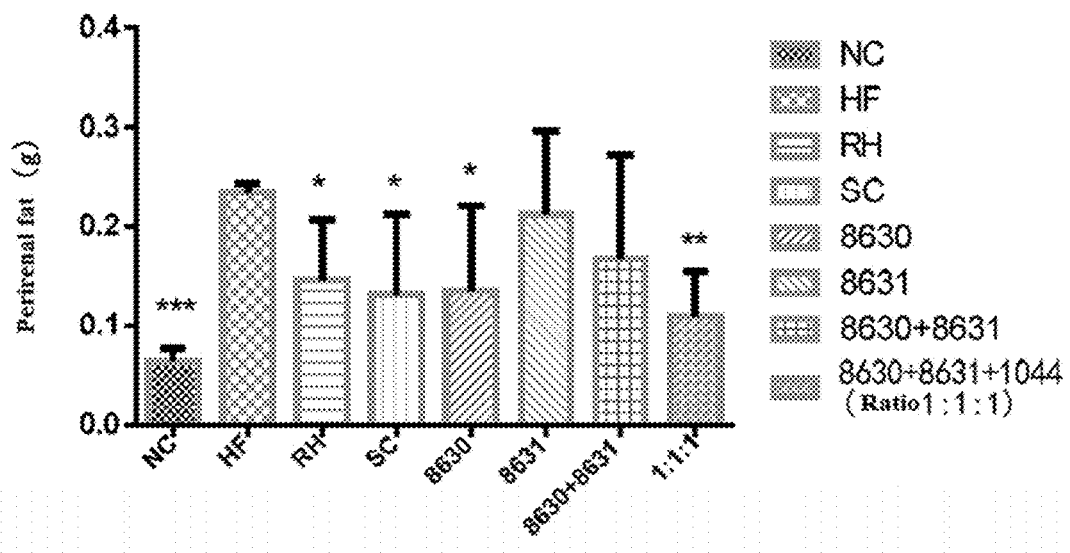
FIG. 2 is a graph showing the effects of different probiotic compounding intervention groups in Example 3 of the present disclosure on alleviating perirenal fat content increasing in mice having high-fat diet induced metabolic syndrome.

At the end of the experiment in 20$^{th}$ week, the mice were fasted, but available to water for 12 h, and anesthetized with ketamine (100 mg/kg bw) by intraperitoneal injection. Blood was collected from the eyeballs, and the mice were sacrificed by dislocation. The blood was centrifuged under conditions of 4° C., 3000 g for 10 min. The supernatant, i.e., the serum, was collected carefully with a small-scale pipette, and froze and stored at −80° C. The epididymis fat (all collected from the left) and the perirenal fat (all collected from the left) were collected and weighted. The liver tissue was rinsed with icy normal saline, and a part of the liver tissue was used to prepare a 10% liver homogenate, which was froze and stored at −80° C. The experimental results were shown in FIG. 1 and FIG. 2.

Compared with the NC group, epididymis fat content in mice having metabolic syndrome in the HF group increased significantly (P<0.0001). In the intervention groups, compared with the HF group, the epididymis fat content of the RH, SC, 8630, 8631, 8630+8631 and 8630+8631+1044 (the ratio of viable count was 1:1:1) groups respectively decreased in an extent of 0.3817 g, 0.3925 g, 0.3067 g, 0.2125 g, 0.21 g and 0.4233 g. The epididymis fat content of the 8630+8631+1044 group (the ratio of viable count was 1:1:1) was lower than that in the drug groups and other probiotic intervention groups. Compared with the 8630 group, 8631 group and 8630+8631 group, the extent of decrease respectively increased by 38.02%, 99.2% and 101.57%, indicating that the CCFM8630+CCFM8631+CCFM1044 had a better effect on decreasing epididymis fat of mice having metabolic syndrome.

Compared with the NC group, perirenal fat content in mice having metabolic syndrome in the HF group increased significantly (P<0.0001). In the intervention groups, compared with the HF group, the perirenal fat content of the RH, SC, 8630, 8631, 8630+8631 and 8630+8631+1044 (the ratio of viable count was 1:1:1) groups respectively decreased in an extent of 0.088 g, 0.102 g, 0.099 g, 0.022 g, 0.0665 g and 0.124 g. The perirenal fat content of the 8630+8631+1044 group (the ratio of viable count was 1:1:1) was lower than that in the drug groups and other probiotic intervention groups. Compared with the 8630 group, 8631 group and 8630+8631 group, the extent of decrease respectively increased by 25.25%, 463.64% and 86.47%, indicating that the CCFM8630+CCFM8631+CCFM1044 had a better effect on decreasing perirenal fat of mice having metabolic syndrome.

In view of this, combination of the three probiotics CCFM8630, CCFM8631 and CCFM1044 shows a significant synergistic effect on decreasing the increase of pididymal fat content and perirenal fat content of mice having high fat diet-induced metabolic syndrome.

Example 4: Influence of Probiotic Composition on Fasting Blood Glucose Level and the Area Under Sugar Tolerance Curve (AUC) of Mouse Having High Fat Diet-Induced Metabolic Syndrome C57BL/6J mice were grouped, modeled and treated in the same manner as those in Example 3. The blood glucose measurement was carried out one week (the 19th week) before the end of the experiment. Blood was collected from the tail of a mouse, and measured with a rapid blood glucose meter and blood glucose test paper. The fasting blood glucose was measured after the mice were subjected to 12 h fasting (free to water) overnight; sugar tolerance was measured by subjecting the mice to fasting overnight for 12 h but free to water, to measure the initial blood glucose (0 min), and then administering the mice with 2 g/kg BW glucose solution, to measure the blood glucose at 30th, 60th and 120th min.

Figure 3:
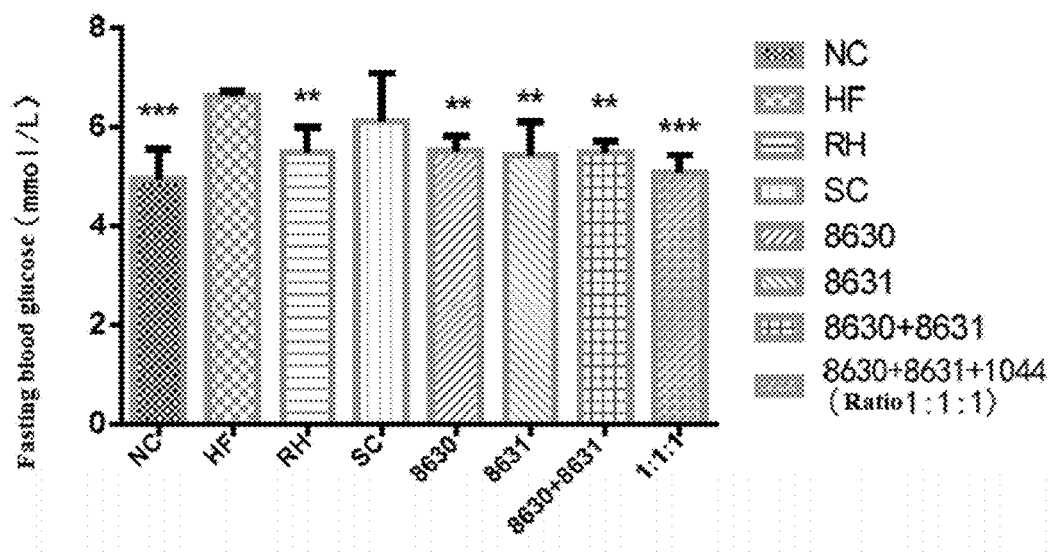
FIG. 3 is a graph showing the effects of different probiotic compounding intervention groups in Example 4 of the present disclosure on alleviating fasting blood glucose level increasing in mice having high-fat diet induced metabolic syndrome.
Figure 4:
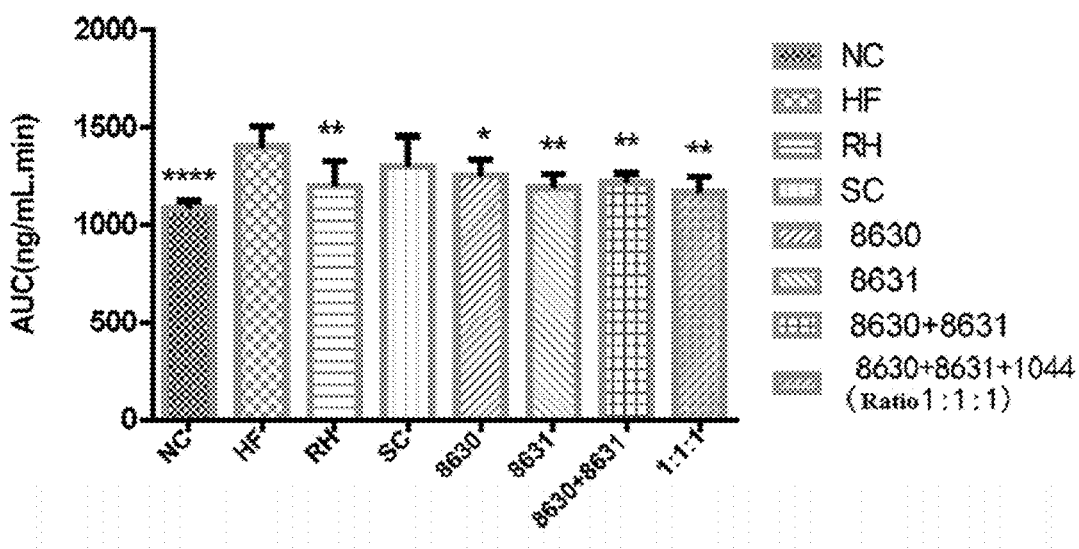
FIG. 4 is a graph showing the effects of different probiotic compounding intervention groups in Example 4 of the present disclosure on alleviating the area under sugar tolerance curve (AUC) increasing in mice having high-fat diet induced metabolic syndrome.

The experimental results were shown in FIG. 3 and FIG. 4. Compared with NC group, fasting blood glucose level in mice having metabolic syndrome in the HF group increased significantly (P<0.0001). In the intervention groups, compared with the HF group, the fasting blood glucose level of the RH, 8630, 8631, 8630+8631 and 8630+8631+1044 (the ratio of viable count was 1:1:1) groups significantly decreased, in an extent of respectivelyl 1.145 mmol/L, 1.125 mmol/L, 1.205 mmol/L, 1.15 mmol/L, 1.55 mmol/L. The fasting blood glucose level of the 8630+8631+1044 group (the ratio of viable count was 1:1:1) was lower than that in the drug groups and other probiotic intervention groups. Compared with the 8630 group, 8631 group and 8630+8631 group, the extent of decrease respectively increased by 37.78%, 28.63% and 34.78%, indicating that the CCFM8630+CCFM8631+CCFM1044 had a better effect on decreasing fasting blood glucose level of mice having metabolic syndrome.

Compared with the NC group, AUC in mice having metabolic syndrome in the HF group increased significantly (P<0.0001). In the intervention groups, compared with the HF group, the AUC of the RH, 8630, 8631, 8630+8631 and 8630+8631+1044 (the ratio of viable count was 1:1:1) groups significantly decreased, in an extent of respectively 204.6, 150, 213, 184.8 and 233.5. The AUC of the 8630+8631+1044 group (the ratio of viable count was 1:1:1) was lower than that in the drug groups and other probiotic intervention groups. Compared with the 8630 group, 8631 group and 8630+8631 group, the extent of decrease respectively increased by 55.67%, 9.62% and 26.35%, indicating that the CCFM8630+CCFM8631+CCFM1044 had a better effect on decreasing AUC of mice having metabolic syndrome.

In view of this, combination of the three probiotics CCFM8630, CCFM8631 and CCFM1044 shows a significant synergistic effect on decreasing the increase of fasting blood glucose level and the area under sugar tolerance curve (AUC) of mice having high fat diet-induced metabolic syndrome.

Figure 5:
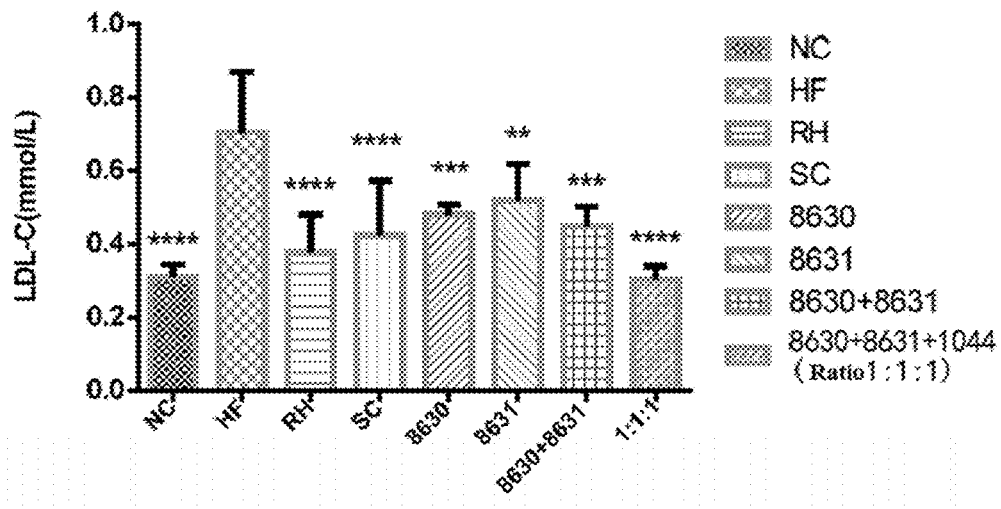
FIG. 5 is a graph showing the effects of different probiotic compounding intervention groups in Example 5 of the present disclosure on alleviating the serum low density lipoprotein (LDL-C) content increasing in mice having high-fat diet induced metabolic syndrome.

Example 5: Influence of Probiotic Composition on Serum Low Density Lipoprotein (LDL-C) of Mouse Having High Fat Diet-Induced Metabolic Syndrome C57BL/6J mice were grouped, modeled and treated in the same manner as those in Example 3. The low density lipoprotein content (LDL-C) in serum was measured according to the detection method of Nanjing Jiancheng low density lipoprotein kit. The experimental results were shown in FIG. 5.

Compared with the NC group, the serum LDL-C content in mice having metabolic syndrome in the HF group increased significantly (P<0.0001). In the intervention groups, compared with the HF group, the LDL-C of the RH, SC, 8630, 8631, 8630+8631 and 8630+8631+1044 (the ratio of viable count was 1:1:1) groups significantly decreased, in an extent of respectively 0.328 mmol/L, 0.28 mmol/L, 0.224 mmol/L, 0.184 mmol/L, 0.256 mmol/L and 0.4 mmol/L. The serum LDL-C content of the 8630+8631+1044 group (the ratio of viable count was 1:1:1) was lower than that in the drug groups and other probiotic intervention groups. Compared with the 8630 group, 8631 group and 8630+8631 group, the extent of decrease respectively increased by 78.57%, 117.39% and 56.25%, indicating that the CCFM8630+CCFM8631+CCFM1044 had a better effect on decreasing serum LDL-C content of mice having metabolic syndrome.

In view of this, combination of the three probiotics CCFM8630, CCFM8631 and CCFM1044 shows a significant synergistic effect on decreasing the increase of serum low density lipoprotein (LDL-C) of mice having high fat diet-induced metabolic syndrome.

Figure 6:
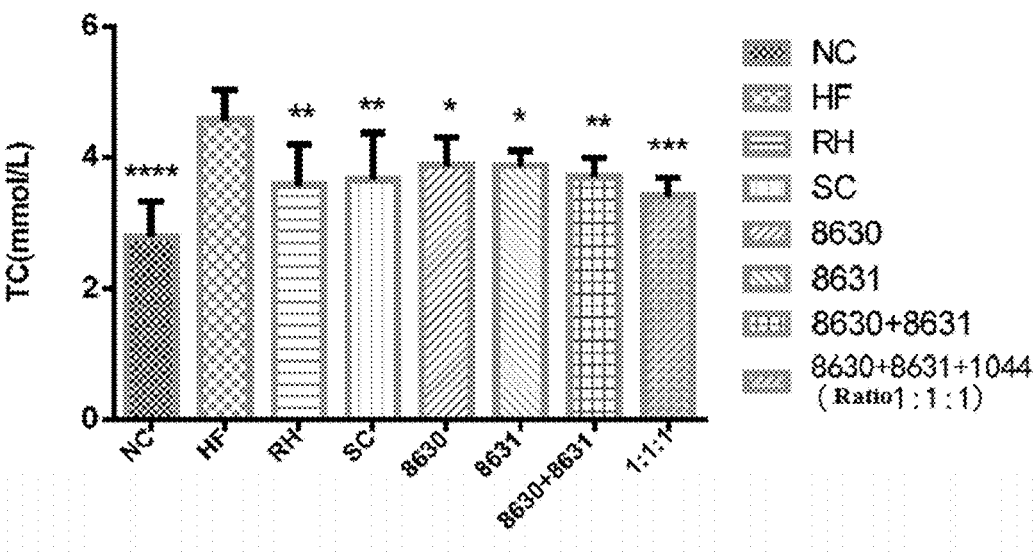
FIG. 6 is a graph showing the effects of different probiotic compounding intervention groups in Example 6 of the present disclosure on alleviating the serum total cholesterol (TC) content increasing in mice having high-fat diet induced metabolic syndrome.

Example 6: Influence of Probiotic Composition on Serum Total Cholesterol (Tc) of Mouse Having High Fat Diet-Induced Metabolic Syndrome C57BL/6J mice were grouped, modeled and treated in the same manner as those in Example 3. The total cholesterol (TC) in serum was measured according to the detection method of Nanjing Jiancheng total cholesterol kit. The experimental results were shown in FIG. 6.

Compared with the NC group, the TC in mice having metabolic syndrome in the HF group increased significantly (P<0.0001). In the intervention groups, compared with the HF group, the TC content of the RH, SC, 8630, 8631, 8630+8631 and 8630+8631+1044 (the ratio of viable count was 1:1:1) groups significantly decreased, in an extent of respectively 0.996 mmol/L, 0.912 mmol/L, 0.696 mmol/L, 0.706 mmol/L, 0.872 mmol/L and 1.16 mmol/L. The TC content of the 8630+8631+1044 group (the ratio of viable count was 1:1:1) was lower than that in the drug groups and other probiotic intervention groups. Compared with the 8630 group, 8631 group and 8630+8631 group, the extent of decrease respectively increased by 66.67%, 64.31% and 33.03%, indicating that the CCFM8630+CCFM8631+CCFM1044 had a better effect on decreasing TC content of mice having metabolic syndrome.

In view of this, combination of the three probiotics CCFM8630, CCFM8631 and CCFM1044 shows a significant synergistic effect on decreasing the increase of serum total cholesterol (TC) of mice having high fat diet-induced metabolic syndrome.

Figure 7:
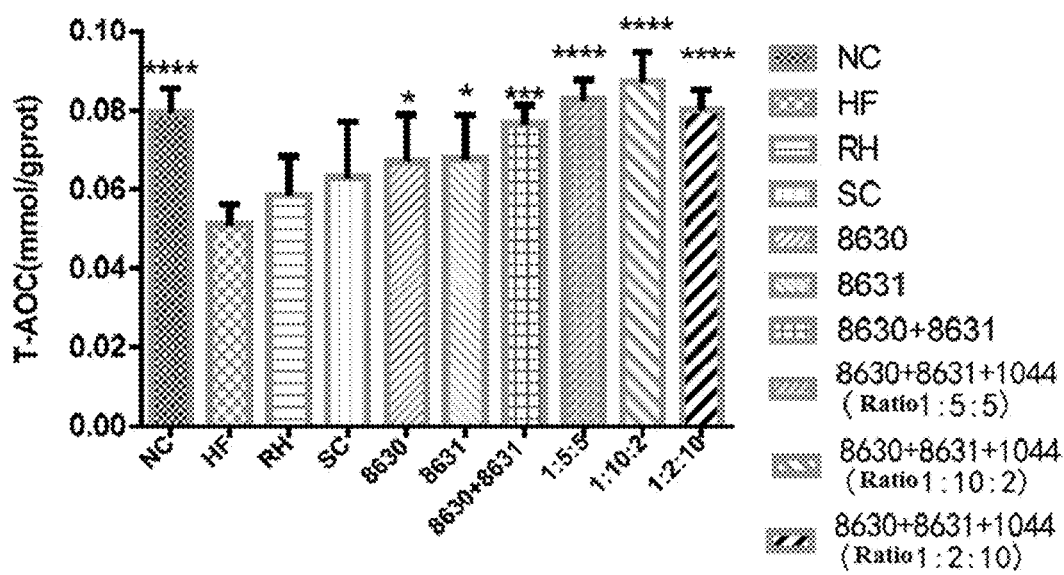
FIG. 7 is a graph showing the effects of different probiotic compounding intervention groups in Example 7 of the present disclosure on alleviating the liver total antioxidant capacity (T-AOC) decreasing in mice having high-fat diet induced metabolic syndrome.
Figure 8:
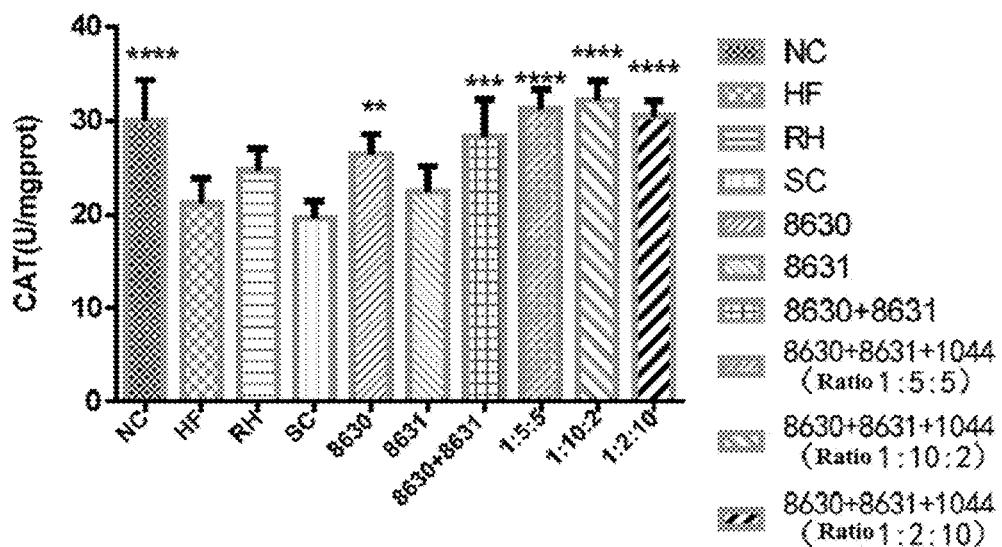
FIG. 8 is a graph showing the effects of different probiotic compounding intervention groups in Example 7 of the present disclosure on alleviating the liver catalase (CAT) content increasing in mice having high-fat diet induced metabolic syndrome.

Example 7: Influence of Probiotic Composition on Liver Total Antioxidant Capacity (T-AOC) and Catalase (Cat) of Mouse Having High Fat Diet-Induced Metabolic Syndrome C57BL/6J mice were modeled in the same manner as that in Example 3. The ratio of viable count of *Bifidobacterium adolescentis* CCFM8630, *Lactobacillus reuteri* CCFM8631 and *Lactobacillus rhamnosus* CCFM1044 were changed from 1:1:1 to 1:5:5, 1:10:2 and 1:2:10, and the total viable count remained to be $1.0 \times 10^9$ CFU/mL. The T-AOC content, CAT content and total protein content in liver homogenate of the mouse were measured according to the detection methods of Nanjing Jiancheng T-AOC kit, CAT kit and total protein kit. The experimental results were shown in FIG. 7 and FIG. 8.

Compared with the NC group, total antioxidant capacity of mice having metabolic syndrome in the HF group decreased significantly (P<0.001). In the intervention groups, compared with the HF group, the total antioxidant capacity of the RH, SC, 8630, 8631, 8630+8631, 8630+8631+1044 (the ratio of viable count was 1:5:5), 8630+8631+1044 (the ratio of viable count was 1:10:2) and 8630+8631+1044 (the ratio of viable count was 1:2:10) groups all increased, in an extent of respectively 0.0075 mmol/g prot, 0.012 mmol/g prot, 0.016 mmol/g prot, 0.0166 mmol/g prot, 0.0256 mmol/g prot, 0.0316 mmol/g prot, 0.0360 mmol/g prot and 0.0292 mmol/g prot. The total antioxidant capacity of each 8630+8631+1044 formulation group was higher than that in the drug groups and other probiotic intervention groups. Compared with the 8630 group, 8631 group and 8630+8631 group, the extent of increase of the 8630+8631+1044 (the ratio of viable count was 1:5:5) group respectively increased by 97.33%, 90.19% and 23.33%. Compared with the 8630 group, 8631 group and 8630+8631 group, the extent of increase of the 8630+8631+1044 (the ratio of viable count was 1:10:2) group respectively increased by 125.25%, 117.11% and 40.78%. Comparing with the 8630 group, 8631 group and 8630+8631 group, the extent of increase of the 8630+8631+1044 (the ratio of viable count was 1:2:10) group respectively increased by 82.50%, 75.90% and 14.06%, indicating that the CCFM8630+CCFM8631+CCFM1044 had a better effect on increasing liver antioxidant capacity of mice having metabolic syndrome.

Compared with the NC group, catalase content of mice having metabolic syndrome in the HF group decreased significantly (P<0.001). In the intervention groups, compared with the HF group, the catalase content of the RH, 8630, 8631, 8630+8631, 8630+8631+1044 (the ratio of viable count was 1:5:5), 8630+8631+1044 (the ratio of viable count was 1:10:2) and 8630+8631+1044 (the ratio of viable count was 1:2:10) groups all increased, in an extent of respectively 3.48 U/mg prot, 5.30 U/mg prot, 1.26 U/mg prot, 7.12 U/mg prot, 10.02 U/mg prot, 10.99 U/mg prot and 9.31 U/mg prot. The catalase content of each 8630+8631+1044 formulation group was higher than that in the drug groups and other probiotic intervention groups. Compared with the 8630 group, 8631 group and 8630+8631 group, the extent of increase of the 8630+8631+1044 (the ratio of viable count was 1:5:5) group respectively increased 89.17%, 692.59% and 40.62%. Compared with the 8630 group, 8631 group and 8630+8631 group, the extent of increase of the 8630+8631+1044 (the ratio of viable count was 1:10:2) group respectively increased 107.55%, 769.62% and 54.29%. Comparing with the 8630 group, 8631 group and 8630+8631 group, the extent of increase of the 8630+8631+1044 (the ratio of viable count was 1:2:10) group respectively increased 75.89%, 636.95% and 30.75%, indicating that the CCFM8630+CCFM8631+CCFM1044 had a better effect on increasing liver catalase content of mice having metabolic syndrome.

In view of this, combination of the three probiotics CCFM8630, CCFM8631 and CCFM1044 shows a significant synergistic effect on increasing the decrease of liver total antioxidant capacity (T-AOC) and total catalase (CAT) of mice having high fat diet-induced metabolic syndrome.

Figure 9:
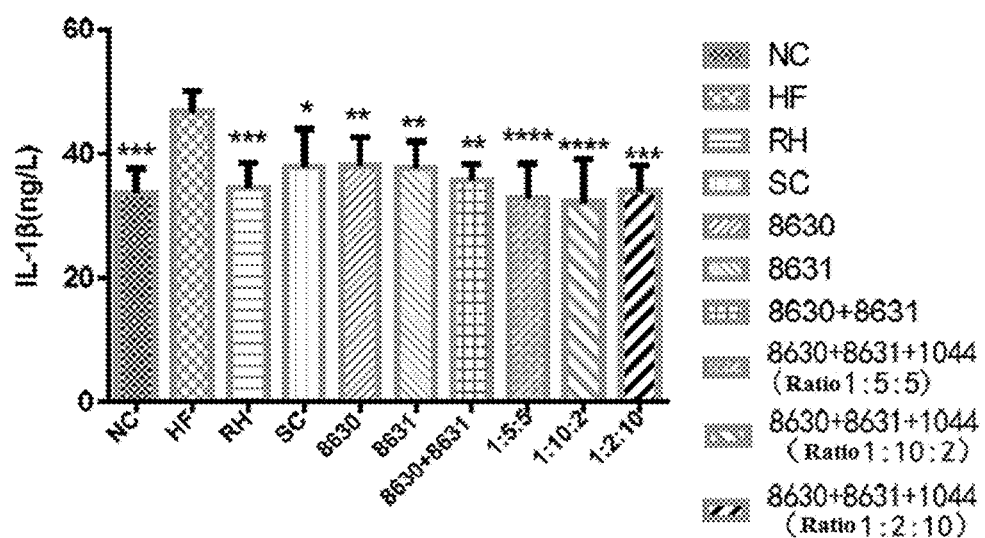
FIG. 9 is a graph showing the effects of different probiotic compounding intervention groups in Example 8 of the present disclosure on alleviating the serum IL-1β content increasing in mice having high-fat diet induced metabolic syndrome. The above figures were plotted with Graphpad Prism5, and comparison among each experimental group was done using LSD test mean comparison. Compared with the model group, if $P<0.05$, it is marked with *. If $P<0.01$, it is marked with . If $P<0.001$, it is marked with *. If $P<0.0001$, it is marked with ****.

Example 8: Influence of Probiotic Composition on Serum IL-1β of Mouse Having High Fat Diet-Induced Metabolic Syndrome C57BL/6J mice were modeled in the same manner as that in Example 3. The ratio of viable count of *Bifidobacterium adolescentis* CCFM8630, *Lactobacillus reuteri* CCFM8631 and *Lactobacillus rhamnosus* CCFM1044 were changed from 1:1:1 to 1:5:5, 1:10:2 and 1:2:10, and the total viable count remained to be $1.0 \times 10^9$ CFU/mL. The IL-1βELISA in serum of mice was measured according to the detection method of Nanjing Senbeijia mouse IL-1βELISA kit. The experimental results were shown in FIG. 9.

Compared with the NC group, serum IL-1β content of mice having metabolic syndrome of HF group increased significantly (P<0.001). In the intervention groups, compared with the HF group, the IL-1β content of the RH, SC, 8630, 8631, 8630+8631, 8630+8631+1044 (the ratio of viable count was 1:5:5), 8630+8631+1044 (the ratio of viable count was 1:10:2) and 8630+8631+1044 (the ratio of viable count was 1:2:10) groups significantly decreased, in an extent of respectively 12.26 ng/L, 8.88 ng/L, 8.79 ng/L, 9.11 ng/L, 11.09 ng/L, 13.85 ng/L, 14.63 ng/L and 12.80 ng/L. The IL-1β content of each formulation group of 8630+8631+1044 was lower than that in the drug groups and other probiotic intervention groups. Compared with the 8630 group, 8631 group and 8630+8631 group, the extent of decrease of the 8630+8631+1044 (the ratio of viable count was 1:5:5) group respectively increased by 57.53%, 52.03% and 24.89%. Compared with the 8630 group, 8631 group and 8630+8631 group, the extent of decrease of the 8630+8631+1044 (the ratio of viable count was 1:10:2) group respectively increased by 66.41%, 60.60% and 31.93%. Compared with the 8630 group, 8631 group and 8630+8631 group, the extent of decrease of the 8630+8631+1044 (the ratio of viable count was 1:2:10) group respectively increased by 45.63%, 40.55% and 15.46%, indicating that the CCFM8630+CCFM8631+CCFM1044 had a better effect on decreasing inflammation of mice having metabolic syndrome.

In view of this, combination of the three probiotics CCFM8630, CCFM8631 and CCFM1044 shows a significant synergistic effect on decreasing the increase of serum IL-1β of mice having high fat diet-induced metabolic syndrome.

The invention claimed is:

1. A probiotic composition, consisting of *Bifidobacterium adolescentis* CCFM8630, *Lactobacillus reuteri* CCFM8631 and *Lactobacillus rhamnosus* CCFM1044; wherein ratio of viable count of the *Bifidobacterium adolescentis* CCFM8630, the *Lactobacillus reuteri* CCFM8631 and the *Lactobacillus rhamnosus* CCFM1044 is 1:(1-10):(1-10).

2. A method for preparing the probiotic composition according to claim 1, comprising, respectively inoculating bacteria solutions of *Bifidobacterium adolescentis* CCFM8630, *Lactobacillus reuteri* CCFM8631 and *Lactobacillus rhamnosus* CCFM1044 to modified MRS culture medium, culturing at 35-37° C. under anaerobic conditions for 18-24h, and collecting thalli; respectively resuspending the thalli with a freeze-drying protective agent so that the content of each thallus is above $10^{10}$ CFU/mL, then culturing the suspension at 37° C. under anaerobic conditions for 40-60 min, drying to obtain freeze-dried bacterial powder of each thallus, resuspending and diluting, and spreading on a plate to determine the viable count in the bacterial powder; and compounding and mixing the freeze-dried bacterial powder of *Bifidobacterium adolescentis* CCFM8630, the freeze-dried bacterial powder of *Lactobacillus reuteri* CCFM8631 and the freeze-dried bacterial powder of *Lactobacillus rhamnosus* CCFM1044 in a certain proportion such that ratio of viable count of the *Bifidobacterium adolescentis* CCFM8630, the *Lactobacillus reuteri* CCFM8631 and the *Lactobacillus rhamnosus* CCFM1044 is 1:(1-10):(1-10).

3. The method according to claim 2, wherein the modified MRS culture medium (mMRS) is an MRS culture medium that contains 0.05% of L-cysteine hydrochloride; the freeze-drying protective agent is an aqueous solution that contains 100 g/L-150 g/L skimmed milk powder, 30 g/L-100 g/L sucrose and 30 g/L-100 g/L trehalose; and the drying is a vacuum freeze drying that is carried out after pre-freezing at −15 to 20° C. for 8 to 14h.

4. A method for alleviating metabolic syndrome, comprising using the probiotic composition according to claim 1.

5. The method according to claim 4, wherein the probiotic composition is in the form of a health care food or a medicine.

6. The method according to claim 5, wherein the health care food is a microbial agent or a fermented food.

7. A microbial agent containing the probiotic composition according to claim 1.

8. The microbial agent according to claim 7, wherein viable count of the probiotic composition is more than $1 \times 10^{11}$ CFU/g.

* * * * *